(12) United States Patent
Suzuki et al.

(10) Patent No.: US 6,584,171 B2
(45) Date of Patent: Jun. 24, 2003

(54) X-RAY IMAGING DETECTOR AND X-RAY IMAGING APPARATUS

(75) Inventors: Masakazu Suzuki, Kyoto (JP); Takeshi Hayashi, Kyoto (JP); Yutaka Ito, Kyoto (JP); Akifumi Tachibana, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 09/789,087

(22) Filed: Feb. 20, 2001

(65) Prior Publication Data

US 2001/0021244 A1 Sep. 13, 2001

(30) Foreign Application Priority Data

Feb. 21, 2000 (JP) ........................................ 2000-043037

(51) Int. Cl.[7] .................................................. H05G 1/64
(52) U.S. Cl. ........................ 378/98.8; 378/196; 378/39
(58) Field of Search ................................ 378/196, 197, 378/98.8, 176, 175, 38–40

(56) References Cited

U.S. PATENT DOCUMENTS 5,848,123 A * 12/1998 Strömmer .................. 378/98.8

FOREIGN PATENT DOCUMENTS

JP 11-104127 * 4/1999 ............ A61B/6/14

* cited by examiner

Primary Examiner—Drew A. Dunn
Assistant Examiner—Chih-Cheng Kao
(74) Attorney, Agent, or Firm—Koda & Androlia

(57) ABSTRACT

An X-ray imaging detector for generating X-ray transmission image in a form of electric signal, for use in X-ray imaging apparatus which comprises the X-ray imaging detector, an X-ray generator and a fixing support for fixedly positioning an object to be examined between the X-ray generator and the X-ray imaging detector mounted thereon, whereby X-ray imaging is performed by moving the X-ray generator and the X-ray imaging detector both interposing the object fixedly positioned by the fixing support while keeping facing each other. The X-ray imaging detector comprises an imaging element for generating electric charged image constituting X-ray transmitted image by detecting X-ray radiated from the X-ray generator and transmitted through the object, a TDI (time delay integration) clock generator for generating TDI clock signal, and a TDI clock controller for controlling generating of TDI clock signal from the TDI clock generator based on TDI frequency control data for controlling the frequency of the TDI clock signal and for executing time delay integration control of the charged image generated by the imaging element corresponding to the TDI clock signal.

11 Claims, 13 Drawing Sheets

(a)

| 1 | 2 | 0 | 2 | 1 | 2 | 2 | 3 |
|---|---|---|---|---|---|---|---|
| 1 | 3 | 2 | 0 | 1 | 2 | 3 | 2 |
| 2 | 0 | 2 | 3 | 0 | 2 | 1 | 3 |
| 1 | 3 | 2 | 0 | 2 | 1 | 3 | 2 |
| 3 | 1 | 2 | 1 | 1 | 2 | 3 | 0 |
| 1 | 2 | 0 | 1 | 0 | 2 | 2 | 3 |
| 3 | 1 | 2 | 2 | 3 | 2 | 0 | 1 |
| 0 | 2 | 0 | 3 | 2 | 1 | 2 | 3 |

(b)

| 07 | 04 | 06 | 10 |
|----|----|----|----|
| 06 | 07 | 05 | 09 |
| 07 | 04 | 05 | 08 |
| 06 | 07 | 08 | 06 |

(c)

| 03 | 00 | 02 | 06 |
|----|----|----|----|
| 02 | 03 | 01 | 05 |
| 03 | 01 | 02 | 05 |
| 02 | 03 | 04 | 02 |

*Fig.8*

X-RAY IMAGING DETECTOR AND X-RAY IMAGING APPARATUS

BACKGROUND OF THE INVENTION

1. Field of the Invention

The present invention relates to a medical X-ray imaging detector and a medical X-ray imaging apparatus so as to take out an image such as X-ray transmitted image of entire jaw in the field of dental surgery, oral surgery and otolaryngology.

2. Prior Art

An X-ray imaging detector using highly sensitive CCD (Charge Coupled Device) image sensor as imaging element comparing to a prior film type one recording X-ray transmitted image on an X-ray film has been used.

In a CCD image sensor, an electric charged image obtained by converting X-ray transmitted through an object into visible light by a scintillator is produced on a light receiver, the electric charged image is output in a form of voltage signal after time delay integrated, and finally A/D converted so as to be taken out as electronic image.

When panoramic X-ray imaging is executed for entire jaw, according to basic principle of imaging, transfer speed of electric charged image generated and accumulated on the CCD image sensor is required to be kept at a speed corresponding to rotational speed of a rotary arm in spite of relatively moving the object and the film at a prescribed speed. Such a principle is known as TDI (Time Delay Integration) imaging as shown in JP-A-61-22841, JP-A-2-84942, and JP-Y-4-48169.

In JP-A-11-104127 and JP-A-11-104218, an X-ray imaging detector which can directly take out an X-ray transmitted image as electronic image by incorporating an A/D converter in a CCD image sensor and an improved X-ray imaging apparatus in which such an X-ray imaging detector has compatibility with a conventional film detector so as to be detachable on a detector holder of an X-ray imaging apparatus have been proposed. Both of them have attempted to execute TDI imaging easily.

However, in the above-mentioned prior arts, an X-ray imaging apparatus is provided with a TDI clock generator and so on for executing TDI imaging and a TDI clock generator isn't provided for an X-ray imaging detector itself. Therefore, a TDI clock generator and so on should be provided for an X-ray imaging apparatus for TDI imaging so that it requires much cost for modifying a conventional film type X-ray imaging apparatus to an X-ray imaging apparatus using a CCD sensor. A technique for achieving TDI imaging at a low cost has been highly desired.

The prior arts have only taught an improved method wherein panoramic imaging producing X-ray transmitted image is produced on X-ray film has been substituted with electronic image, or an X-ray generator and an X-ray detector are moved interposing an object. Such prior art hasn't shown method wherein imaging time is speeded up and electronic image for adequate diagnosis is obtained.

The advantage of executing panoramic X-ray imaging at high speed is in that image out of focus caused by moving of an object is solved by shortening imaging time. Moreover, X-ray amount radiated on the object can be restrained and it is useful for reducing X-ray exposed dose amount.

SUMMARY OF THE INVENTION

The present invention has been made to solve the above problems. The first object of the invention is to provide an X-ray imaging detector wherein TDI (Time Delay Integration) imaging using an imaging element such as CCD can be executed even if an X-ray imaging apparatus isn't provided with a TDI clock generator.

The second object of the invention is to provide an X-ray imaging detector for executing high speed imaging, which is an ultimate object wherein suitable method hasn't been proposed in conventional TDI imaging using an imaging element such as CCD for obtaining X-ray image.

The third object of the invention is to provide an X-ray imaging detector which can generate electronic images with different resolutions by altering imaging mode according to diagnostic purposes.

Further object of the invention is to provide an X-ray imaging detector which is user-friendly improved from the view point of user in order to achieve the above-mentioned first to third objects.

Moreover, the other object of the invention is to provide a medical X-ray imaging apparatus which can achieve the above-mentioned objects by itself.

In order to solve the above-mentioned problems, the applicant of the present invention proposes an X-ray imaging detector, an X-ray imaging apparatus having an X-ray imaging detector, and an X-ray imaging apparatus having a function of an X-ray imaging detector by itself.

The present invention proposes an X-ray imaging detector for generating X-ray transmitted image in a form of electric signal for use in an X-ray imaging apparatus in which the X-ray imaging apparatus comprises an X-ray generator and a fixing means for fixedly positioning an object to be examined between the X-ray generator and the X-ray imaging detector mounted thereon, whereby X-ray imaging is performed by moving the X-ray generator and the X-ray imaging detector both interposing the object fixedly positioned by the fixing means while keeping facing each other. The X-ray imaging detector comprises an imaging element for generating electric charged image constituting X-ray transmitted image by detecting X-ray radiated from the X-ray generator and transmitted through the object, a TDI clock generator for generating TDI clock signal, and a TDI clock controller for controlling generating of TDI clock signal from the TDI clock generator based on TDI frequency control data for controlling the frequency of the TDI clock signal and for executing TDI control of the electric charged image generated by the imaging element corresponding to the TDI clock signal.

This X-ray imaging detector itself is provided with the TDI clock generator and the TDI clock controller and is a autonomic type detector of which imaging mode is such that the imaging element can be TDI controlled without receiving supply of TDI clock signal from the X-ray imaging apparatus. Therefore, if the TDI clock generator isn't provided for the X-ray imaging apparatus, TDI imaging can be achieved so that the above-mentioned first object can be accomplished.

A CCD imaging sensor is preferably used for an imaging element, however, any device can be used if it can execute TDI control.

According to the above-mentioned X-ray imaging detector of the present invention, the TDI clock controller may be provided with a clock control data memory storing the TDI frequency control data.

In such an X-ray imaging detector, the TDI clock controller has the clock control data memory. Therefore, it is convenient that the TDI frequency control data which has been stored by a manufacturer beforehand can be taken out from the memory and TDI imaging can be executed.

According to the above-mentioned X-ray imaging detector of the present invention, the clock control data memory may rewritablly store the TDI frequency control data.

In such an X-ray imaging detector, the clock control data memory is rewritable and the TDI frequency control data can be rewritten by a manufacturer at the time of shipment in order to meet the product specification of the X-ray imaging apparatus. Therefore, it is convenient that appropriate TDI imaging can be executed in compliance with the X-ray imaging apparatus when a manufacturer attaches the X-ray imaging detector on the X-ray imaging apparatus.

The control data memory is preferably constructed with a flash memory and EEPROM. However, any device can be used if stored data is rewritable and is kept even if an electric source is shut off.

According to the above-mentioned X-ray imaging detector of the present invention, the clock control data memory may store plural patterns of the TDI frequency control data.

In such an X-ray imaging detector, such control as enlarged imaging, maxillary antrum imaging, jaw joint imaging and selection of adult or child can be executed by storing plural patterns of TDI frequency control data in case of panoramic imaging using an X-ray imaging apparatus provided with an X-ray imaging detector. It is very convenient and can accomplish the above-mentioned third object.

According to the above-mentioned X-ray imaging detector of the present invention, a selection means for selecting at least one of the plural patterns of TDI frequency control data stored in the clock control data memory may be further provided.

In such an X-ray imaging detector, TDI frequency control data can be selected by the selection means from the memory storing plural patterns of TDI clock signal so that the above-mentioned third object can be accomplished.

A doctor or an operator may use such a selection means corresponding to the signal of the selection means provided for a controller of the X-ray imaging apparatus or such a selection means may be pre-set by a manufacturer before shipment.

According to the above-mentioned X-ray imaging detector of the present invention, the TDI clock controller may be further provided with binning function when the electric charged image generated by the imaging element is TDI controlled.

The binning function means that the electric charged image produced on the imaging element is summed by real-time operation as it is.

In such an X-ray imaging detector, binning can be executed so as to heighten sensitivity of the sensor and the data amount transmitted to an A/D converter is reduced. Therefore, TDI controlled X-ray imaging can be achieved at high speed without replacing with high speed A/D converter and memory amount for processing picture image for X-ray imaging can be reduced so that the above-mentioned second object can be accomplished.

According to the above-mentioned X-ray imaging detector of the present invention, the TDI clock controller may be further provided with function of moving the X-ray generator and the X-ray imaging detector at high speed while keeping facing each other by executing binning function when the electric charged image generated by the imaging element corresponding to the TDI clock signal is TDI controlled.

In such an X-ray imaging detector, the electric charged image is integrated by binning and the electric charged image with enough contrast can be obtained by small amount of X-ray. Utilizing this, the X-ray generator and the X-ray imaging detector are moved at high speed and X-ray is radiated for a short time. Therefore, X-ray imaging can be executed at higher speed and X-ray exposed dose amount of the object can be reduced without changing the X-ray imaging apparatus itself. Furthermore, the problem of picture out of focus caused by movement of the object is resolved so that the above-mentioned second object can be accomplished.

According to the above-mentioned X-ray imaging detector of the present invention, the TDI clock controller may selectively execute at least normal projection mode and high-speed projection mode which is faster than the normal mode when the electric charged image generated by the imaging element may be TDI controlled and in each projection mode frequency of the TDI clock signal and binning data may control elements.

In such an X-ray imaging detector, it is convenient for an operator that normal projection mode and high speed imaging mode can be selectively executed and each imaging mode can be preferably executed because the frequency of the TDI clock signal and binning information are control element.

According to the above-mentioned X-ray imaging detector of the present invention, an imaging element for producing X-ray transmitted image may be a CCD sensor of full frame transfer type.

In such an X-ray imaging detector, FFT (full frame transfer type) CCD censor is used as an imaging element. By using the characteristic of the sensor in which there is no accumulation part and a light receiving part is enlarged that much, it is preferably achieved for a measurement of slow frame rate, for example TDI X-ray imaging of the present invention.

The present invention proposes an X-ray imaging apparatus provided with the above-mentioned X-ray imaging detector.

Such an X-ray imaging apparatus is provided with the above-mentioned detector so that the same effect as the above-mentioned detector can be achieved.

According to the X-ray imaging apparatus of the present invention, the TDI clock signal produced from the TDI clock generator provided for the X-ray imaging detector and movement control signal for moving the X-ray generator and the X-ray imaging detector both interposing the object fixedly positioned by the fixing means while keeping facing each other are varied in synchronizing manner.

In such an X-ray imaging apparatus, the TDI clock signal of the X-ray imaging detector is synchronized with movement control signal of the X-ray imaging apparatus so that X-ray imaging for executing TDI imaging can be preferably accomplished.

According to the X-ray imaging apparatus of the present invention, the X-ray imaging apparatus may be a panoramic X-ray imaging apparatus.

As the X-ray imaging apparatus is constructed as a panoramic imaging apparatus, the effect of the above-mentioned X-ray imaging apparatus can be brought out in case of panoramic imaging.

According to the X-ray imaging apparatus of the present invention, the X-ray imaging apparatus may be a cephalometric X-ray imaging apparatus.

As the X-ray imaging apparatus is constructed as a cephalometric imaging apparatus, the effect of the above-mentioned X-ray imaging apparatus can be brought out in case of cephalometric imaging.

The present invention proposes an X-ray imaging apparatus comprising an X-ray generator, an X-ray imaging detector, and a fixing means for fixedly positioning an object to be examined between the X-ray generator and the X-ray imaging detector mounted thereon, whereby X-ray imaging is performed by moving the X-ray generator and the X-ray imaging detector both interposing the object fixedly positioned by the fixing means while keeping facing each other. The X-ray imaging detector comprises an imaging element for producing electric charged image constituting X-ray transmitted image by detecting X-ray radiated from the X-ray generator and transmitted through the object. The X-ray imaging apparatus comprises a TDI clock generator for generating TDI clock signal, a clock control data memory storing TDI frequency control data for controlling frequency of TDI clock signal generated from the TDI clock generator, and a TDI clock controller for controlling generating of TDI clock signal from the TDI clock generator based on TDI frequency control data for controlling the frequency of the TDI clock signal and for executing TDI control of the electric charged image generated by the imaging element corresponding to the TDI clock signal. The TDI clock controller is further provided with function of moving the X-ray generator and the X-ray imaging detector at high speed while keeping facing each other by executing binning processing when the electric charged image generated by the imaging element corresponding to the TDI clock signal is TDI controlled.

The X-ray imaging apparatus is provided with the above-mentioned TDI clock generator, the above-mentioned TDI clock controller, the above-mentioned clock control data memory at the X-ray imaging apparatus side. And the TDI clock controller can execute high speed imaging using the above-mentioned binning operation. Therefore, if these parts are provided for the X-ray imaging detector, the apparatus can bring out the same effect as the above-mentioned detector so that high speed binning X-ray imaging apparatus of heteronomic type is achieved.

According to the X-ray imaging apparatus of the present invention, the TDI clock controller may selectively execute at least normal projection mode and high-speed projection mode which is faster than the normal mode when the electric charged image generated by the imaging element is TDI controlled and in each projection mode frequency of the TDI clock signal and binning data may be employed as control elements.

Such an X-ray imaging apparatus is provided with the same function of the above-mentioned X-ray imaging detector on the apparatus side so that the same effect of the X-ray imaging detector can be brought out even if such function isn't provided for the detector side.

According to the X-ray imaging apparatus of the present invention, an imaging element for producing X-ray transmitted image may be a CCD sensor of FFT (full frame transfer) type.

In such an X-ray imaging apparatus imaging element is FFT type CCD sensor like the above-mentioned X-ray imaging detector so that the same effect as the X-ray imaging detector can be achieved.

According to the X-ray imaging apparatus of the present invention, the TDI clock signal generated from the TDI clock generator provided for the X-ray imaging detector and movement control signal for moving the X-ray generator and the X-ray imaging detector both interposing the object fixedly positioned by the fixing means while keeping facing each other may be varied in synchronizing manner.

In such an X-ray imaging apparatus, the TDI clock signal of the X-ray imaging detector is synchronized with the movement control signal of the X-ray imaging apparatus so that TDI X-ray imaging can be preferably achieved.

According to the X-ray imaging apparatus of the present invention, the X-ray imaging apparatus may be a panoramic X-ray imaging apparatus.

As the X-ray imaging apparatus is constructed as a panoramic imaging apparatus, the effect of the above-mentioned X-ray imaging apparatus can be brought out in case of panoramic imaging.

According to the X-ray imaging apparatus of the present invention, the X-ray imaging apparatus may be a cephalometric X-ray imaging apparatus.

As the X-ray imaging apparatus is constructed as a cephalometric imaging apparatus, the effect of the above-mentioned X-ray imaging apparatus can be brought out in case of cephalometric imaging.

BRIEF DESCRIPTION OF THE DRAWINGS

FIGS. 8a, b, c explains idea of the X-ray transmitted image obtained by the X-ray imaging detector of the present invention.

DETAILED DESCRIPTION OF THE INVENTION

Now the preferable embodiments of the present invention will be described hereinafter referring to the attached drawings.

Figure 1:
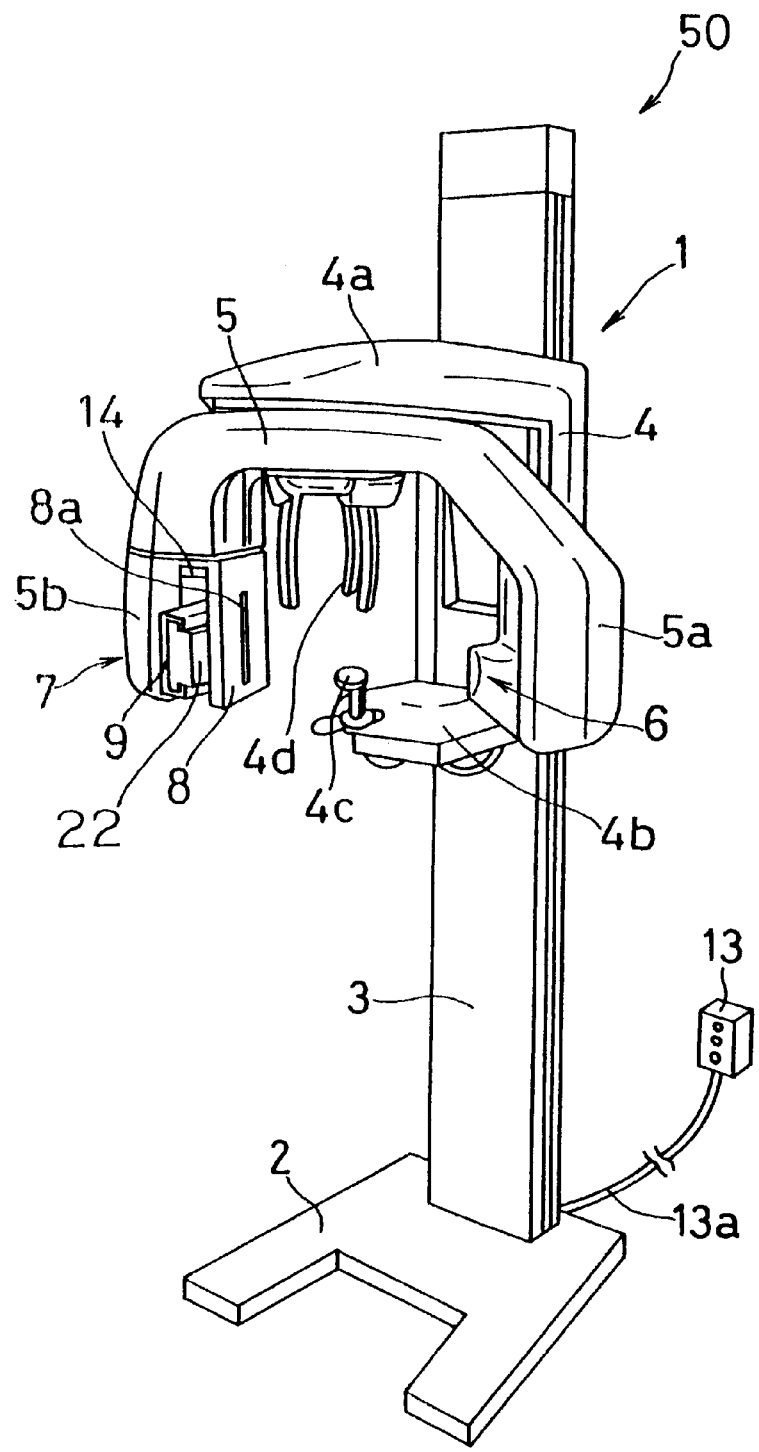
FIG. 1 shows perspective view of outer appearance of an X-ray imaging apparatus having an X-ray imaging detector of the present invention.
Figure 2:
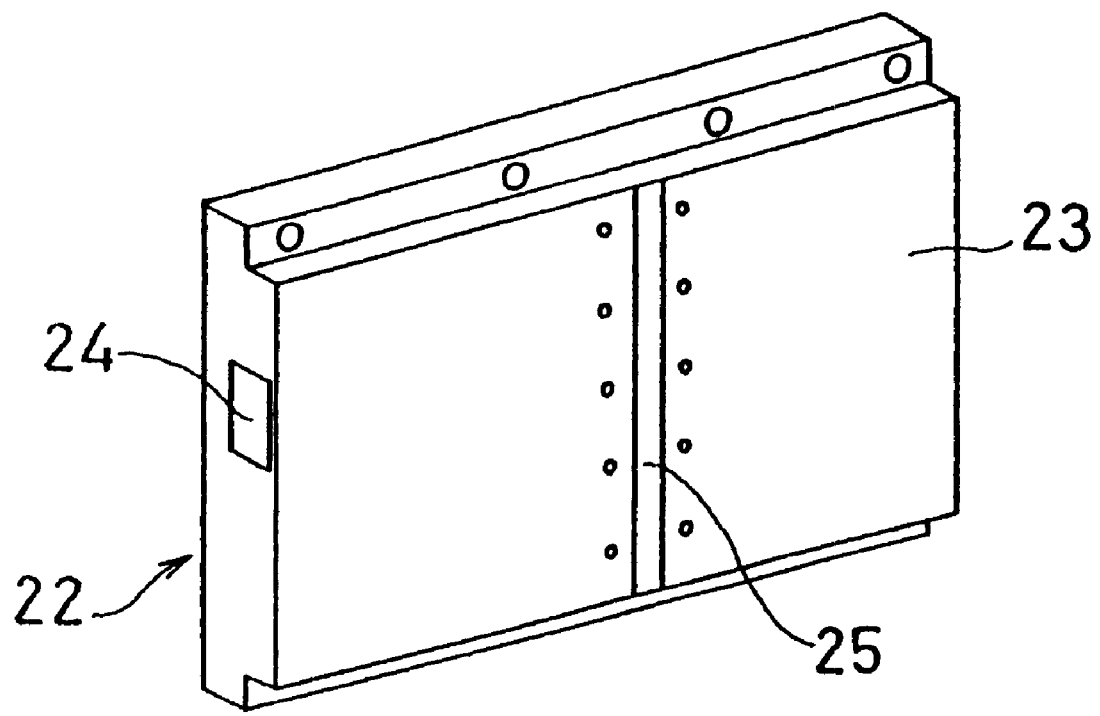
FIG. 2 is an outer perspective view of the X-ray imaging detector shown in FIG. 1.
Figure 3:
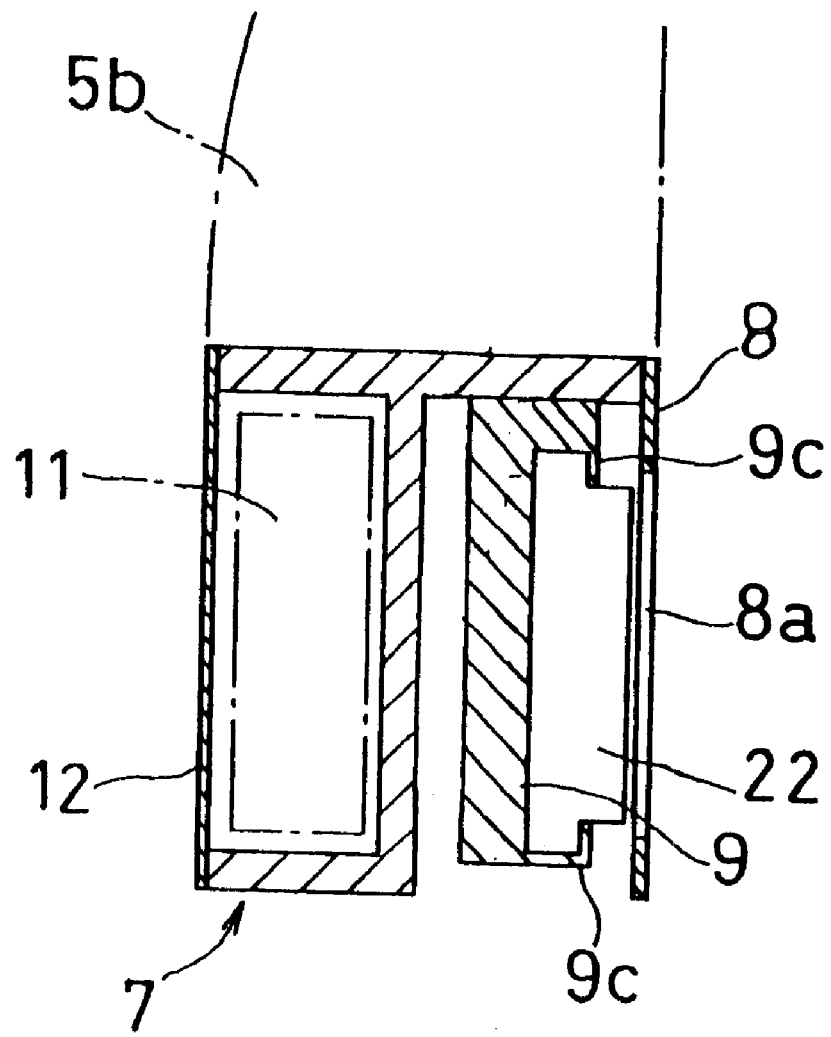
FIG. 3 is a sectional view of substantial part showing an attachment part for the X-ray imaging detector of the X-ray imaging apparatus shown in FIG. 1.

FIG. 1 shows outer appearance of an X-ray imaging apparatus having an X-ray imaging detector of the present invention. FIG. 2 shows outer appearance of the X-ray imaging detector and FIG. 3 shows a sectional view of an attachment part for the X-ray imaging detector of the X-ray imaging apparatus shown in FIG. 1.

The X-ray imaging apparatus 50 is a panoramic X-ray imaging apparatus. A support pillar 3 stands on a base 2 of a body 1 of the apparatus, a support body 4 is provided for the support pillar 3 so as to be movable up and down, and a rotary arm 5 is rotatably attached to the support body 4. A support arm 4a and a patient frame 4b both of which extend horizontally are provided at the upper end and the lower end of the support body 4 respectively. A chin rest 4c is provided for the patient frame 4b.

The support arm 4a houses an XY table which is freely movable in X-direction or Y-direction by a step motor and the rotary arm 5 is designed to be suspended via the XY table so as to move horizontally at random. The reference mark 4d is a patient's head presser of a patient fixing means fixed by penetrating the rotary arm 5 under the support arm 4a and is provided with positioning control mechanism.

The rotary arm 5 is provided with rotary mechanism for rotating the rotary arm 5 against the support arm 4a by a step motor and is constructed so as to be rotated around the vertical axis line while moving the center of rotation by means of the XY table.

The both sides of the rotary arm 5 are pendent and an X-ray generator 6 is provided for one side 5a and an X-ray detection part 7 is provided for the other end 5b so as to oppose the end 5a. The X-ray generator 6 is provided with an X-ray tube, an X-ray shield having a vertical first slit, and a control mechanism for changing the shape of the first slit (all of them aren't shown).

The X-ray detection part 7 is provided with a vertical second slit 8a corresponding to the first slit and the shield plate 8 having control mechanism of the slit 8a so as to oppose the X-ray generator 6. A detector holder 9 is provided at the back of the X-ray detection part 7 and an X-ray imaging detector 22 is attached to the detector holder 9.

The detector holder 9 is provided with a pair of guides 9c at its up and bottom for mounting the X-ray imaging detector 22 detachably as shown in FIG. 3. The guides 9c are designed to mount conventional film type detector detachably. When the detector 22 is detachable for the apparatus body and the size of the detector 22 is the same as that of conventional film type detector, such an apparatus can also serve as film type imaging apparatus. The X-ray imaging detector 22 may be directly fixed into the X-ray detection part 7 without using the detector holder 9.

At the back of the X-ray detection part 7A are control part 11 of the apparatus body comprising a print board incorporating several kinds of circuit and so on and an operation panel 12 covering the outside of the control part 11. Several switches and liquid crystal display (not shown) are provided for the operation panel 12.

The body 1 is provided with a remote control box 13 connected via a code 13a and a main switch for turning on and off electric current source and an X-ray radiating switch are provided for the box 13. The X-ray detection part 7 is provided with a connector 14 for connecting the X-ray imaging detector 22.

As shown in FIG. 2 the X-ray imaging detector 22 is armored with a housing 23 accommodating the electric X-ray detector (not shown) and corresponding several circuits and a connector 24 is provided at one side of the housing 23 for connecting outer circuit. The connector 24 is usually connected by means of a cable (not shown) in which electric supply line and a signal line are unified between the connector 14 of the X-ray detection part 7, however, it can be used for connecting external devices such as personal computer.

The housing 23 is constructed with suitable material having required strength such as metal like aluminum plate and synthetic resin like ABS resin. An X-ray receiving part 25 made of such material that has preferable permeability and blocks off visible light, like dark color ABS resin, is vertically provided at the back of the second slit 8a and the electric X-ray image detector is provide therein.

Figure 4:
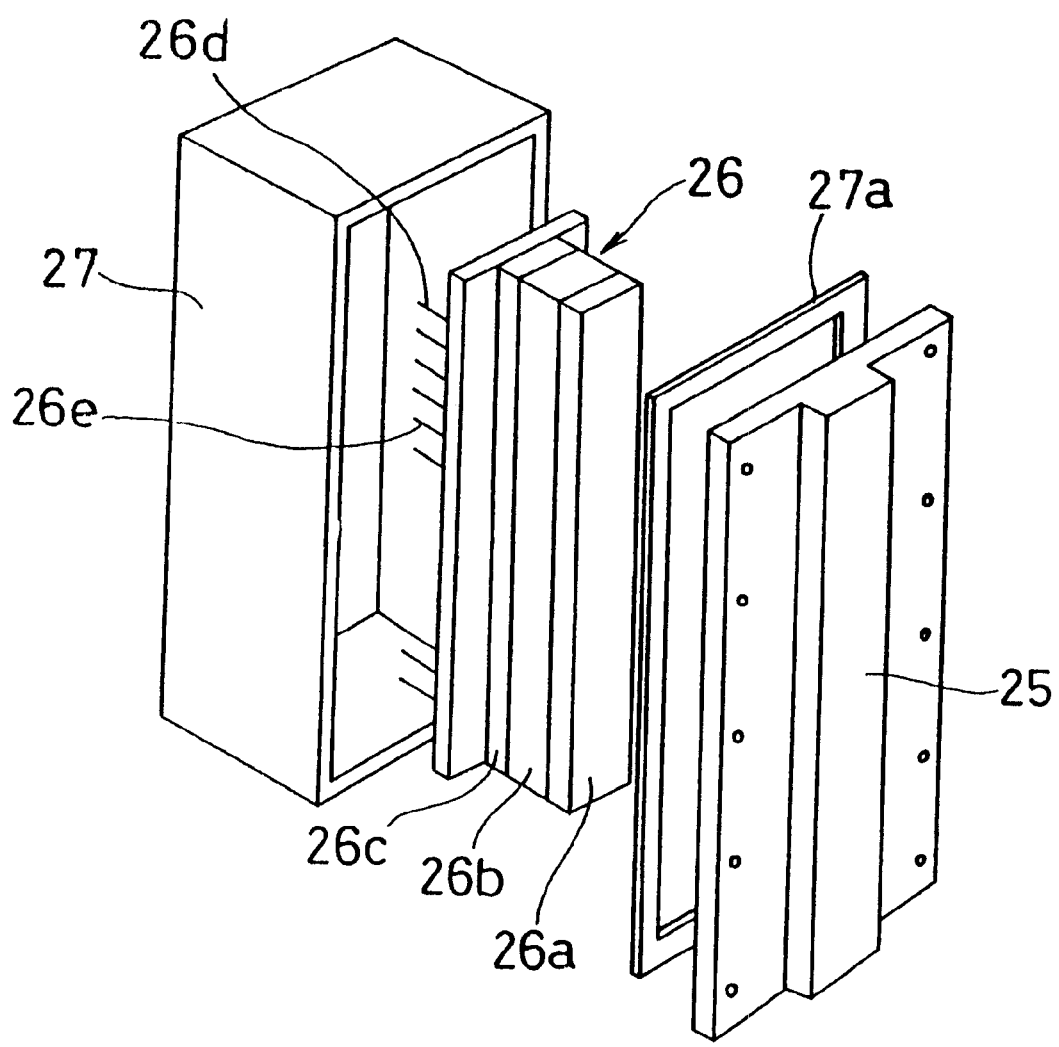
FIG. 4 is an exploded perspective view of the electric X-ray image detector incorporated in the X-ray imaging detector shown in FIG. 2.

FIG. 4 shows the electric X-ray image detector 26 housed in the X-ray imaging detector.

The electric detector 26 is arranged at the back of the X-ray receiving part 25 and is provided with an illuminant (scintillator) 26a for converting the radiated X-ray into visible light, an optical fiber 26b for transmitting the illumination of the illuminant 26a into a light receiving surface of the imaging element 26c, and the imaging element 26c described hereinafter. The reference numeral 27 is a protector case, 27a is a sealing material, and 26d is a signal pin of the imaging element 26c.

Figure 5:
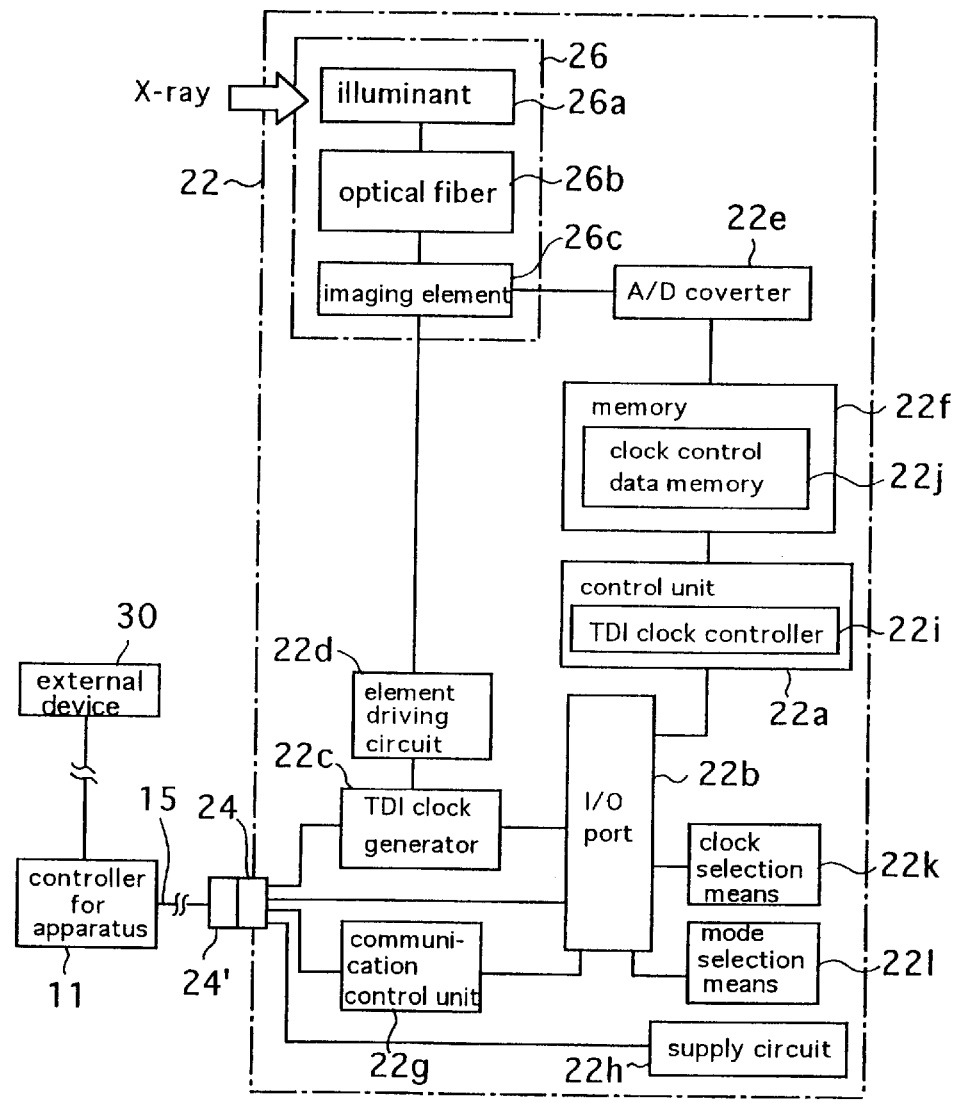
FIG. 5 is a block diagram showing schematic construction of substantial parts of the X-ray imaging detector shown in FIG. 2.

FIG. 5 is a block diagram showing schematic construction of substantial parts of one embodiment of the X-ray imaging detector of the present invention.

The X-ray imaging detector 22 is provided with a control unit 22a constructed with MPU (CPU) which controls the operation of each circuit in the detector 22 and the operation of the whole apparatus including the apparatus body (shown in FIG. 1) by itself or by being combined with the control part 11 of the apparatus body, an input/output port 22b, a TDI clock generator 22c for generating TDI clock signal, a driven circuit for an imaging element 22d, an A/D converter 22e, a memory 22f, a communication control circuit 22g, and a power supply circuit 22h. These circuits, the electric X-ray image detector 26 and the connector 24 are connected as shown in the figure.

The detector 22 is used by mounting to the X-ray imaging apparatus body (not shown) detachably or fixedly. The connector 24 is electrically and controllably connected to the apparatus body by means of a connector 24' provided for a cable 15 introduced from the control part 11 of the body. The control part 11 is designed to be connected with an external device 30 comprising a personal computer and so on in order to input control data into the control part 11 and the detector 22 or to output and store the data.

The detector 22 may be designed to output digital signal by A/D converting therein or an A/D converter may be housed in the apparatus body 1 in such a manner that analog signal is output from the detector 22 and is converted into digital signal in the apparatus body 1.

The electric X-ray image detector 26 is comprised of the illuminant 26a, the optical fiber 26b and the imaging element 26c and outputs X-ray transmitted image in the form of voltage signal. Its basic function is well known and will be explained hereinafter.

The characteristic of the detector 22 is in that it is provided with the above-mentioned TDI clock generator 22c therein, it generates TDI clock signal from the TDI clock generator 22c based on the TDI frequency control data for controlling the frequency of the TDI clock signal, a control unit 22a is provided for a TDI clock control means 22i for TDI controlling the electric charged image generated on the imaging element corresponding to the TDI clock signal, and a clock control data memory 22j storing TDI frequency control data is provided for the memory 22f.

The detector 22 itself has a TDI clock generator and a TDI clock controller so that it serves as a autonomic type detector wherein TDI control of the imaging element can be achieved without being supplied with TDI clock signal from the X-ray imaging apparatus. Therefore, if a TDI clock generator isn't provided for the X-ray imaging apparatus body, TDI imaging can be accomplished. As the result, TDI imaging is possible by replacing with the detector of the present invention if the X-ray imaging apparatus doesn't constructed for TDI imaging so that large industrial effect can be obtained.

Further according to the detector 22, it is convenient that TDI control mode imaging can be executed by taking out the TDI frequency control data which has been pre-stored by a manufacturer from the memory 22j because the TDI clock control means 22i is provided with the clock control data memory 22j. When the clock control data memory 22j is constructed to be rewritable, the TDI frequency control data can be rewritten so as to meet the product specification of the X-ray imaging apparatus at the time of shipment from a manufacturer so that it is convenient an operator can execute TDI control mode imaging corresponding to the apparatus only by mounting the detector on the apparatus.

The control data memory 22j is preferably constructed with a flash memory and EEPROM. However, any device can be used if stored data is rewritable and is kept even if an electric source is shut off.

A plural patterns of TDI frequency control data are stored in the memory 22j and the detector 22 is provided with a clock selection means 22k for selecting desired pattern from the plural patterns. Therefore, if the X-ray imaging apparatus having the detector 22 is a panoramic imaging apparatus, such control as enlarged imaging, maxillary antrum imaging, jaw joint imaging and selection of adult or child can be executed so that usability is improved.

When the electric charged image produced on the imaging element 26c is TDI controlled, binning is executed and a mode selection means 22l is provided for selecting at least normal imaging mode and high speed imaging mode capable of higher speed imaging so as to selectively execute either mode. In each imaging mode, the frequency of TDI clock signal and data for binning are set as control element. Therefore, it is convenient for an operator and each imaging mode can be preferably executed. Binning will be explained later.

Figure 6:
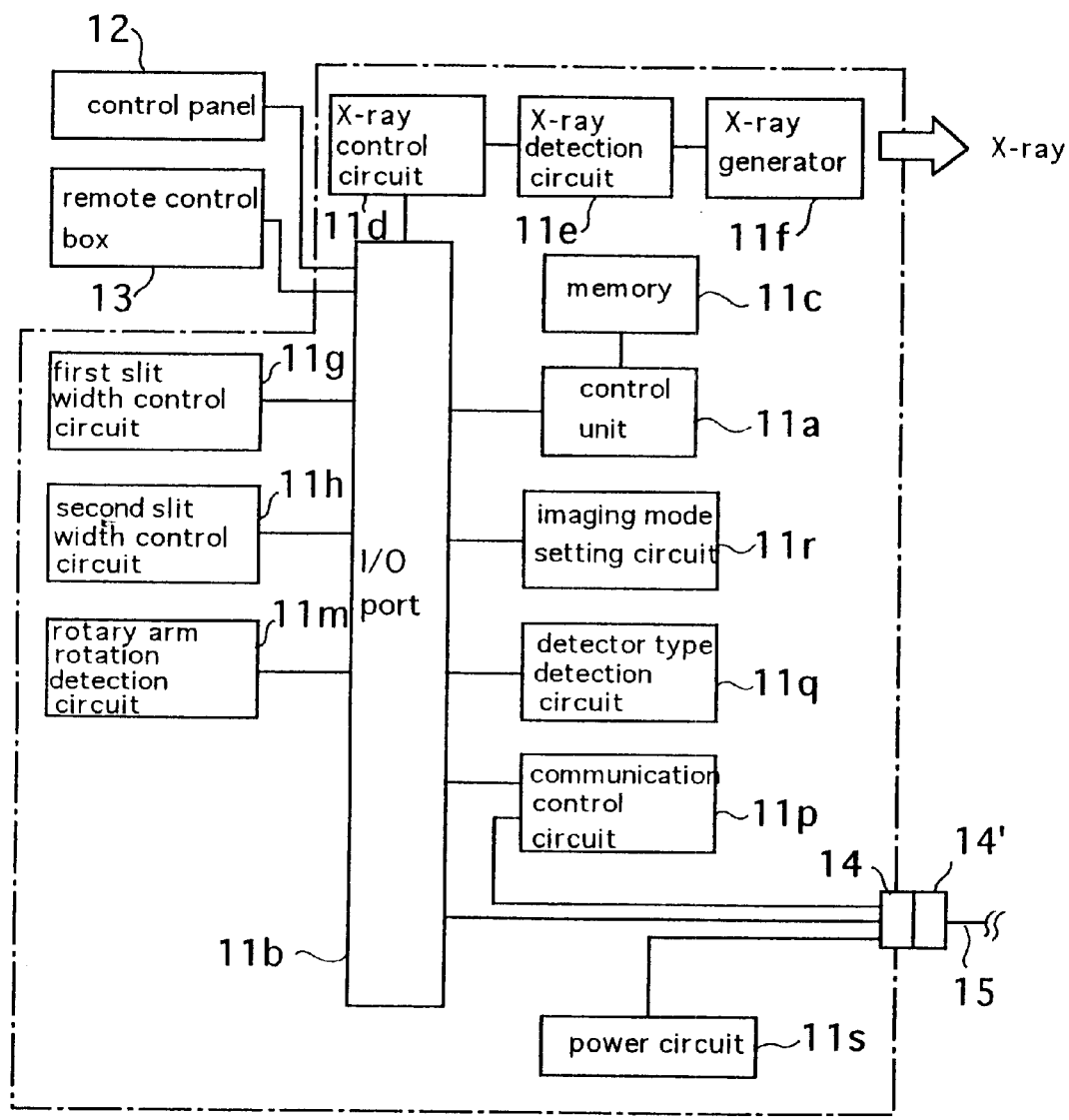
FIG. 6 is a block diagram showing schematic construction of substantial parts of the controller in the X-ray imaging apparatus having X-ray imaging detector shown in FIG. 5.

FIG. 6 is a block diagram showing schematic construction of substantial parts of the controller in the X-ray imaging apparatus having X-ray imaging detector shown in FIG. 5. The same parts as the above-mentioned have the same numerals and their explanation is omitted.

The control part 11 is provided with a control unit 11a constructed with MPU (CPU) which serves as a center of operational control of the entire apparatus, an input/output port 11b, and a memory 11c. There are also an X-ray radiation control circuit 11d, an X-ray radiation detection circuit 11e, an X-ray generator 11f, a first slit width adjustment circuit 11g, a second slit width adjustment circuit 11h, a rotary arm rotation detection circuit 11m, an imaging mode setting circuit 11r, a detector type detection circuit 11q, a communication control circuit 11p, and a power supply circuit 11s. They are connected to the control unit 11a via the input/output port 11b.

A connector 14 corresponding to a connector 14' of a connecting cable 15 for connecting with the X-ray imaging detector 22 of FIG. 5 is provided. The input/output port 11b, the communication control circuit 11p, and the power supply circuit 11s are connected to the connector 14.

An operation panel 12 for inputting operational data and a remote control box 13 for inputting the same data from remote place are connected to the input/output port 11b.

The control part 11 doesn't include a TDI clock generator required for X-ray imaging of TDI control mode. However, TDI control mode X-ray imaging can be executed by mounting the above-mentioned X-ray imaging detector 22 and electrically and controllably connecting via the connecting cable 15.

That is, a conventional X-ray imaging apparatus without a TDI clock generator can achieve TDI control mode X-ray imaging if the X-ray imaging detector of the present invention is used.

The X-ray imaging detector of the present invention is characterized in that it includes a TDI clock generator and TDI clock control means required for TDI control mode X-ray imaging. Other construction elements are almost the same as that of conventional X-ray imaging detector. Accordingly it is different in that the X-ray imaging apparatus doesn't need a TDI clock generator and the other construction elements are the almost the same as conventional apparatus.

Figure 7:
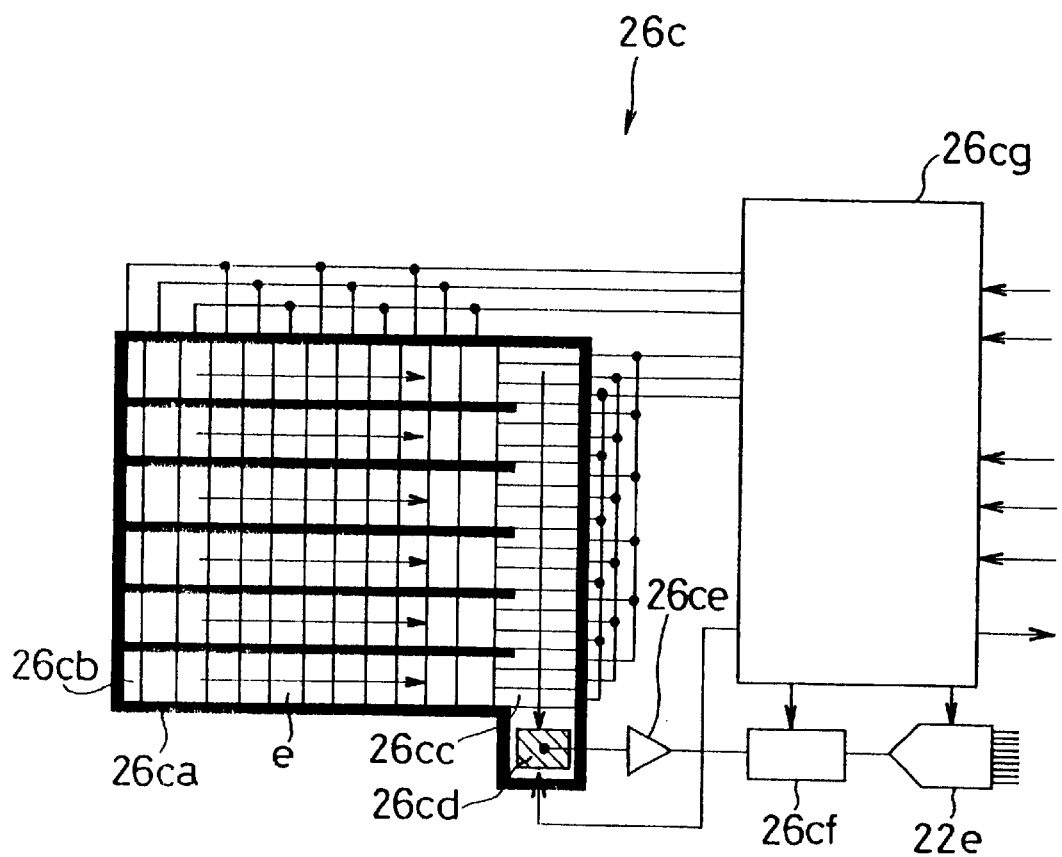
FIG. 7 shows schematic construction of the imaging element provided for the X-ray imaging detector shown in FIG. 2.

FIG. 7 shows schematic construction of the imaging element provided for the X-ray imaging detector shown in FIG. 2 and FIG. 4.

The imaging element 26c is constructed with a FFT type (Full Frame Transfer type) CCD image sensor. The numeral 26ca is a sensor matrix constructing a light receiving part and is constructed such that a horizontal shift register 26cb transferring electric charge horizontally is formed on plural rows up and down. Pixels e arranged on rows and columns are formed by potential wells produced on the horizontal shift register 26cb.

The numeral 26cc is an associative shift register for accumulating and combining the electric charged image transferred simultaneously, horizontally and juxtapositionally via the potential well of the horizontal shift register 26cb constructed in plural columns vertically. The numeral 26cd is an output well for further vertically accumulating and combining the associative electric charged image which is serial transferred from the associative shift register 26cc in vertical direction. And the numeral 26ce is am amplifier for further converting the associated electric charged image sequentially output from the output well 26cd and for outputting as a sensor signal.

The sensor signal output from the amplifier 26ce is zero compensated by a zero-offset compensation circuit 26f and then delivered to the A/D converter 22e. The numeral 26cg is a controller for delivering and controlling necessary control signal including TDI clock signal for transferring and binning the electric charged image to the shift register, the associative shift register, and the output well all of which construct a CCD image sensor.

The basic operation of electric charge transfer of a CCD image sensor wherein signal electric charge obtained by lightening is blocked in the potential well of the sensor matrix 26ca comprising a light receiving surface so as to be transferred in semiconductor is well known in JP-A-9-200625 and so on. Therefore, binning of signal electric charge and high speed process of TDI clock which are characteristic of the present invention will be explained hereinafter.

According to the present invention, it is required to transfer the electric charged image in the imaging element at high speed in case of medical panoramic X-ray imaging such as dental use wherein the rotary arm 5 in FIG. 1 is rotated at high speed. For this purpose the electric charged image accumulated on the light receiving surface of the imaging element is transferred by a TDI clock signal of higher speed frequency. When the electric charged image produced in the CCD sensor is voltage transferred and output as a sensor signal to the A/D converter as it is, the A/D converter is required to convert analog signal to digital signal at high speed corresponding to such high speed transfer. Therefore, the ability of the sensor is required to be improved so that the entire construction of the X-ray imaging apparatus has to be modified.

The easiest method in order to solve the above-mentioned problem is that one part of the sensor signal output from the CCD sensor in the form of analog signal is skipped so as to reduce output interval of the sensor signal output to the A/D converter from the CCD sensor. However, rough digital image lacking information is obtained because such obtained sensor signal lacks some parts.

The binning operation adopted in the present invention can solve such a problem. Important information as image doesn't drop off and electric charge transfer of the CCD sensor can be speeded up according to the rotational speed of the rotary arm so that imaging time can be shortened by binning operation.

When X-ray transmitted image hits on the illuminant 26*a* (see FIG. 4), X-ray is converted into visible light and the visible light produces electric charged image on the sensor matrix 26*ca* of the imaging element 26*c* via optical fiber 26*b*. When the imaging element 26*c* receives TDI clock signal, the electric charged imaged produced on the sensor matrix 26*ca* is transferred at one time in vertically column from the first column to the last column (called signal electric charge of column hereinafter) while being blocked in the potential well (TDI control).

When such signal electric charge of column is transferred to the associative shift register 26*cc*, plural columns of signal electric charge are accumulated and associated according to pre-set binning data. For example, when binning data is set so as to bin 3×3 pixel and 4×4 pixel, signal electric charge of three columns and four columns meaning combination of column direction is accumulated and associated and the accumulated and associated electric charged image is transferred to the next output well 26*cd*.

When the electric charged image is transferred to the output well 26*cd* from the associative shift register 26*cc* (called signal electric charge of row hereinafter), three rows and four rows of signal electric charge meaning combination in row direction are accumulated and associated if binning data is set so as to do bin 3×3 pixel and 4×4 pixel.

Associated electric charge is sequentially transferred to the output well 26*cd* from the associative shift register 26*cc* until one time transfer of row electric charge accumulated and associated in the associative shift register is finished. The output well 26*cd* accumulates the number of binning in row direction of the electric charge transferred from the associative shift register 26*cc* and clears the electric charge remained in the output well 26*cd* each time of outputting. By repeating such operations, it is designed such that remaining unnecessary electric charge isn't added on the associated electric charge sequentially transferred from the associative shift register 26*cc*.

When such electric charge transferred to the associative shift register 26*cc* from the sensor matrix 26*ca* and accumulated as the number of binning in column direction specified by binning data is transmitted to the output well, the associative shift register 26*cc* accumulates electric charged signal of the specified rows by the binning number in row direction. Then electric charge of the accumulated and associated rows is sequentially transferred to the output well 26*cd* and the output well 26*cd* accumulates and associates the specified number of electric charge by the binning number in column direction to be output.

According to such binning, the output well 26*cd* adds plural TDI pixels blocked by the potential well of the sensor matrix 26*ca* on a new pixel and outputs while the pixels are kept electric charged. Therefore, time interval of the sensor signal output from the A/D converter after being voltage converted from the output well 26*cd* becomes long like the added parts are skipped.

Consequently, so much higher speed process isn't required for the latter A/D converter 22*e*. As the result of binning, when transfer speed of the data output from the CCD sensor is adjusted to process capacity of existing A/D converter 22*e* beforehand, it may be enough that only the frequency contained in TDI frequency control data of the X-ray imaging detector 22 is changed.

In this case it is most important that there is an advantage that the added electric charged image doesn't lack information as X-ray transmitted image consisting integrated data because it includes electric charged image consisting its construction element in integrated form and data process and data storage can be facilitated because total number of pixel as digital image can be reduced.

FIG. 8 explains idea of the X-ray transmitted image obtained by the X-ray imaging detector of the present invention. FIG. 8(*a*) is an original image and each grid shows electric charge of each pixel. When binning is executed for 2×2 pixel based on the original image, the electric charges of the area surrounded by thick lines in 2×2 pixel are added so that an image shown in FIG. 8(*b*) is obtained.

In such a manner binning is to add both rows and columns, only rows, or only columns in a 2×2, or 3×3 square pixel or 2×3 or 3×4 rectangle pixel or to add appropriate number of pixels in one row or one column.

FIG. 8(*c*) shows zero-offset in which after binning shown in FIG. 8(*b*), "4" is subtracted from each area after as to be the smallest electric charge "04" among the all area to be "0". When such zero-offset operation is executed, noise element caused by dark current included in the electric charge element of the pixel so that image becomes clear and dynamic range is increased.

As shown from the figure, the total number of pixel of the original image is reduced corresponding to binning data and consequently the image is reduced. On the other hand, all the electric charged image data of each pixel of the original image is accumulated and used as an element of output X-ray transmitted image so that there is no lack of information caused by skipping pixels.

Figure 9:
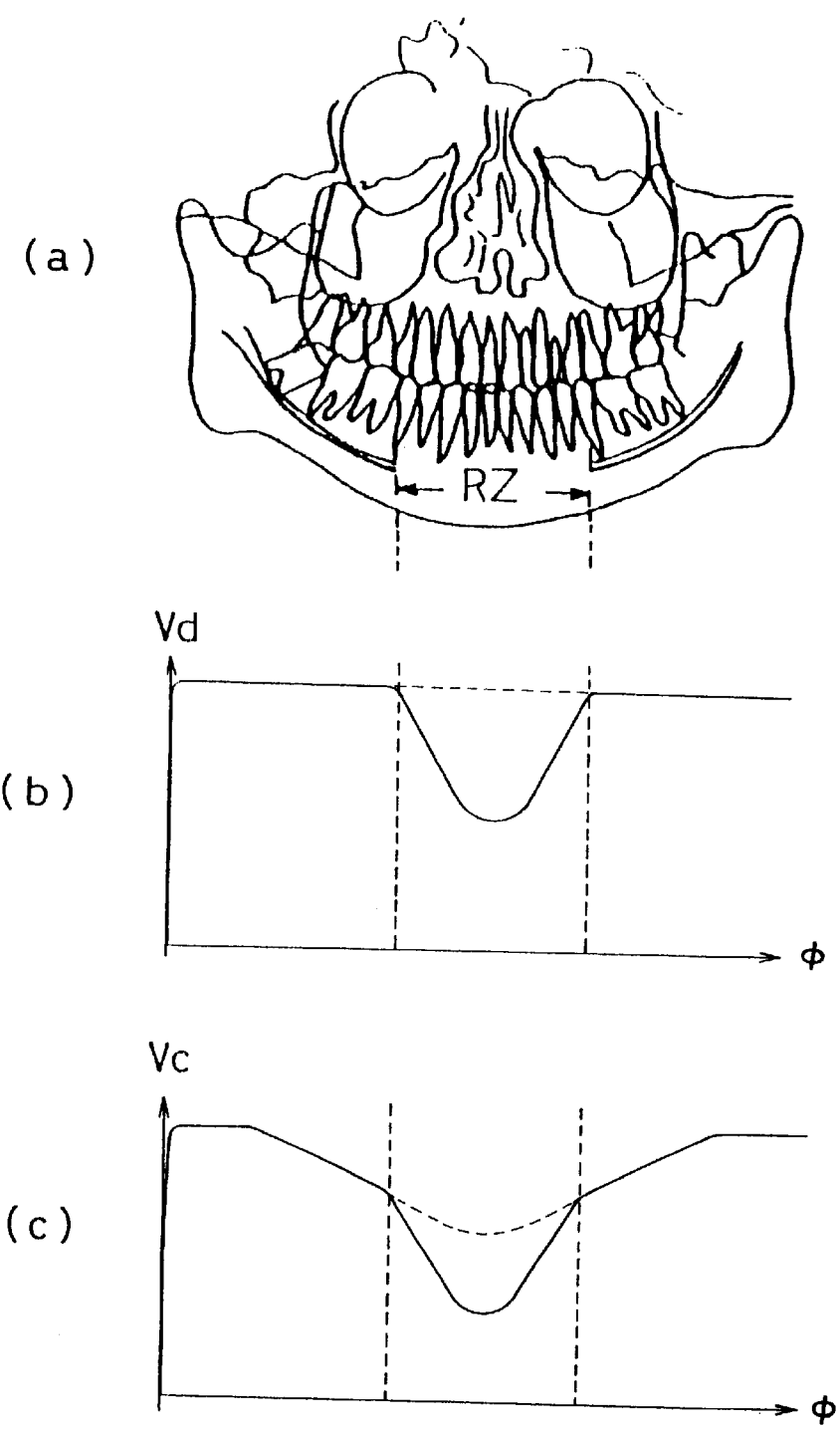
FIGS. 9a, b, c explains idea of the TDI clock signal control data obtained by the X-ray imaging detector of the present invention.

FIG. 9 explains idea of the TDI clock signal control data obtained by the X-ray imaging detector of the present invention.

FIG. 9(*a*) shows an X-ray transmitted image of the entire jaw produced by a panoramic X-ray imaging apparatus provided with an X-ray imaging detector of the present invention. FIG. 9(*b*) is a graph showing rotational speed of the rotary arm to obtain the image. FIG. 9(*c*) is a graph showing the variation of the frequency of corresponding TDI clock signal.

In FIG. 9(*a*) RZ shows an area for compensating density normally applied for panoramic X-ray imaging. In the area RZ X-ray is designed to radiate longer so as to eliminate affect of shade of obstacle such as cervix so that the rotary arm is rotated slowly.

In FIG. 9(b) the longitudinal axis Vd shows rotary speed of the rotary arm, the horizontal axis Ø shows rotary angle of the rotary arm, the solid line shows the speed when compensation is done in the density compensation area RZ, and the broken line shows the speed when compensation isn't done.

In FIG. 9(c) the longitudinal axis Vc is the frequency of TDI clock signal, the horizontal axis Ø shows rotary angle of the rotary arm, the solid line shows the speed when compensation is done in the density compensation area RZ, and the broken line shows the speed when compensation isn't done. The frequency Vc of TDI clock signal corresponds to the TDI control speed of the electric charged image produced on the imaging element and also corresponds to transfer speed of the conventional film type detector.

As shown in the figures, a prescribed relation is existed between the rotational speed Vd of the rotary arm and the frequency Vc of TDI clock signal. Such relation is TDI clock signal control data. The same panoramic X-ray transmitted image of the entire jaw as obtained by moving a conventional film type detector in accordance with the rotational speed Vd of the rotary arm can be obtained by the X-ray imaging detector of the present invention by controlling the frequency of TDI clock signal using the TDI clock signal control data.

The TDI clock signal control data is required to be prepared respectively corresponding to the curve of the rotary speed Vd of the rotary arm as shown in FIG. 9. The curve of the rotary speed Vd of the rotary arm is varied by an X-ray imaging apparatus, imaging purpose, and imaging object. It is convenient that plural patterns of TDI clock signal control data are prepared accordingly in so as to be selected at medical site.

As shown those figures the rotation of the rotary arm and the TDI clock signal are required to be synchronized whereby preferable X-ray transmitted image can be obtained.

When speeding up by binning as mentioned before is executed, the frequency of the TDI clock signal is speeded up in accordance with binning data and correspondingly TDI clock signal control data is prepared.

Figure 10:
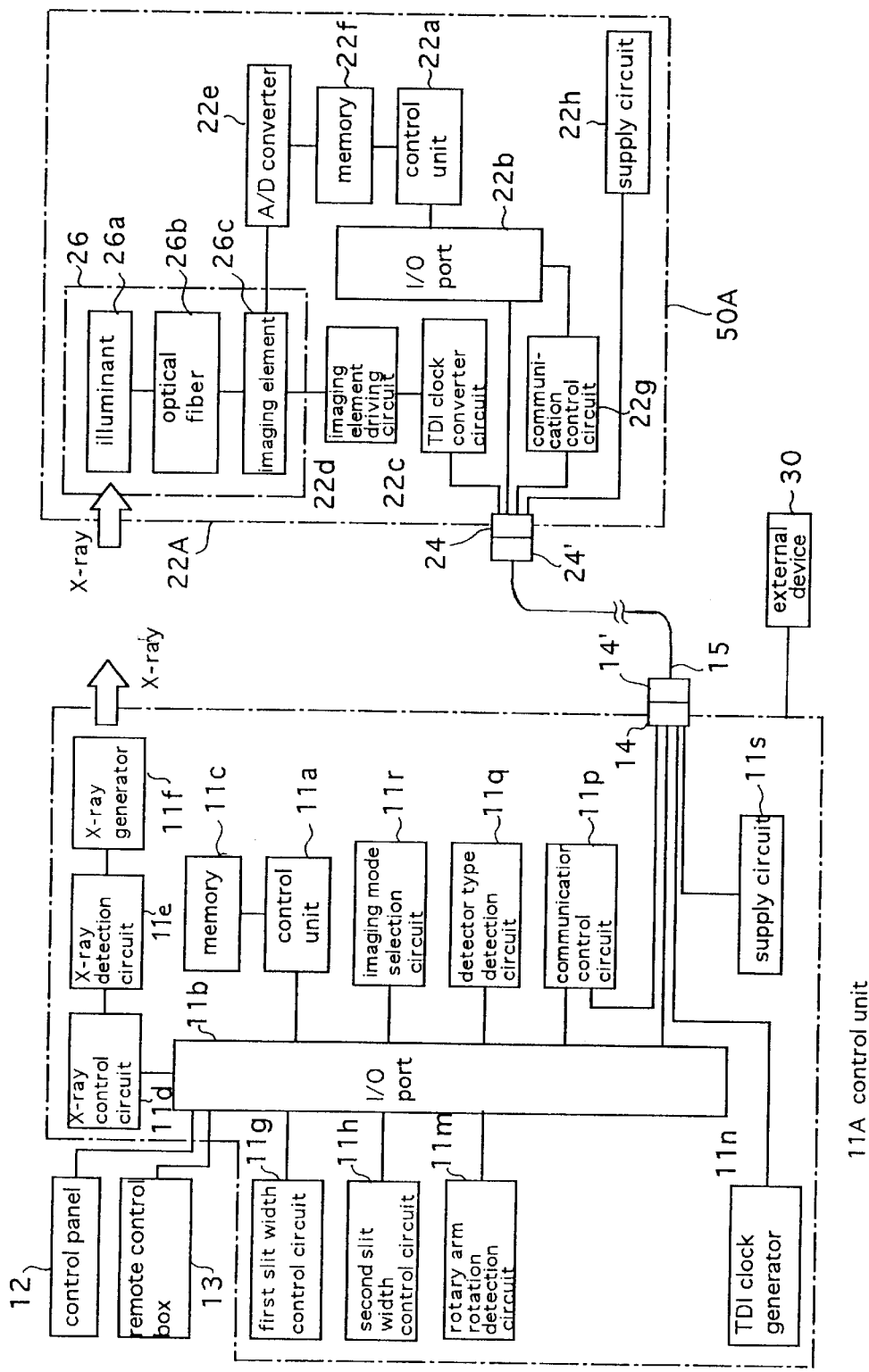
FIG. 10 is a block diagram showing schematic construction of substantial parts of other embodiment of the X-ray imaging apparatus of the present invention.

FIG. 10 is a block diagram showing schematic construction of substantial parts of other embodiment of the X-ray imaging apparatus of the present invention.

According to the X-ray imaging apparatus 50A, comparing to the X-ray imaging apparatus 50 in FIG. 1, a TDI clock generator 11n is provided for a control part 11A of the apparatus body, not for an X-ray imaging detector 22A. In contrast a TDI clock converter circuit 22m for converting the signal from the TDI clock generator is provided for the detector 22A. Corresponding parts like the TDI clock control means 22i, the clock control data memory 22j, the clock selection means 22k, and the mode selection means 22l provided for the X-ray imaging detector 22 in FIG. 1 are provided for the control part 11A of the apparatus body, although they aren't shown in the figure.

According to such an X-ray imaging apparatus 50A, TDI control X-ray imaging can be achieved by using an existing X-ray imaging detector 22A without having the TDI clock generator like the case when the X-ray imaging detector 22 having the TDI clock generator and similar effect can be brought out.

Further according to the apparatus 50A, imaging mode can be selected from heteronomic type (seen from the detector) for TDI imaging using TDI clock generator provided for the apparatus body and self drive mode (see from the detector) for TDI imaging using the TDI clock generator provided for the detector 22, even if the X-ray imaging detector 22 having the TDI clock generator is mounted.

Figure 11:
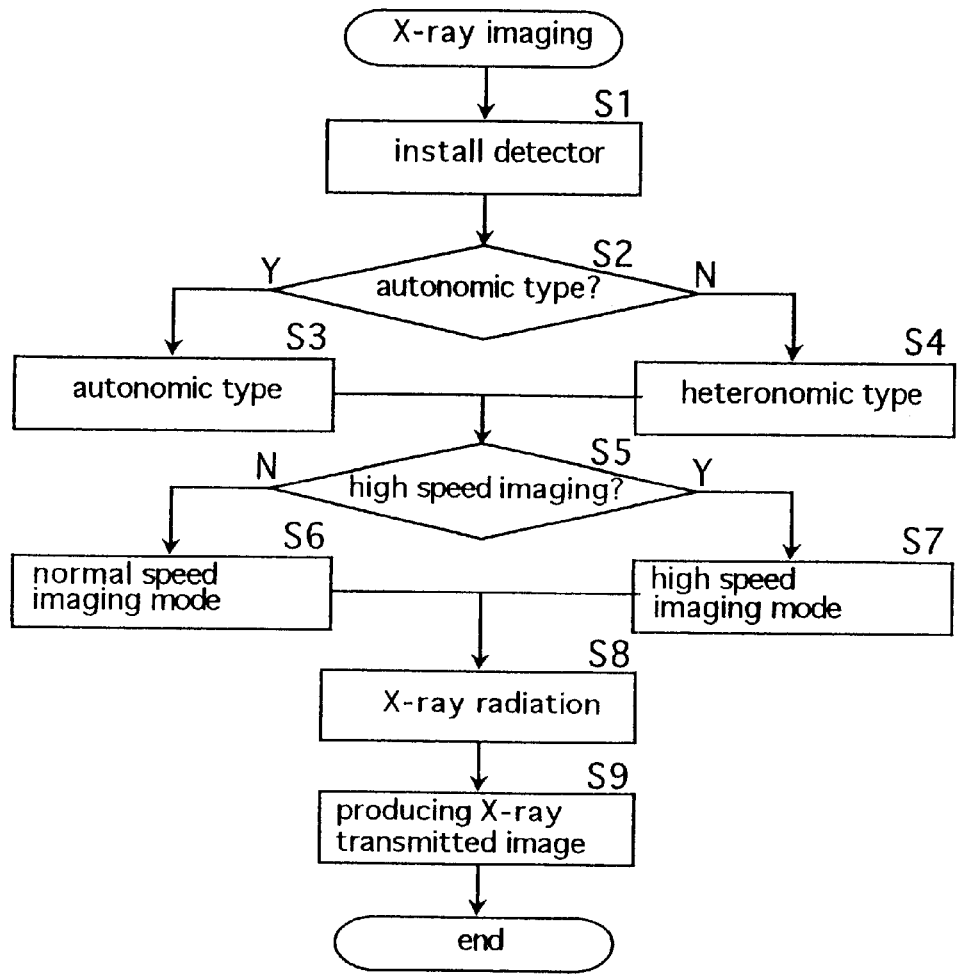
FIG. 11 is a flow chart showing procedure of X-ray imaging using the X-ray imaging detector of the present invention.

FIG. 11 is a flow chart showing procedure of X-ray imaging using the X-ray imaging detector of the present invention.

This flow chart shows basic operation of the X-ray imaging apparatus in which selection of heteronomic type and self mode and selection of normal imaging mode and high speed imaging mode can be possible.

When the X-ray imaging detector is mounted on a detector holder, the X-ray imaging apparatus determines self mode or heteronomic type by reading the existence of the TDI clock generator of the X-ray imaging detector, the content of the TDI frequency control data stored in the clock control data memory, or the characteristic showing the kinds provided for the X-ray imaging detector or by being based on the selection of the mode selection means (S1, S2).

Consequently either mode is set (S3, S4) and TDI frequency control data is read out corresponding to each mode and TDI clock signal frequency pattern according to the rotational speed of the rotary arm is prepared.

Whether normal imaging mode or high speed imaging mode is decided based on the selection by the selection means (S5, S6, S7), and corresponding set is executed. Large frequency is set for the TDI clock signal based on binning data at high speed imaging mode.

When the X-ray imaging apparatus receives radiation command signal, it radiates X-ray on the object while rotating the rotary arm at a speed corresponding to the TDI clock signal modified by a control parameter (S8), X-ray transmitted image is generated on the imaging element as electric charged image in the X-ray imaging detector, the image is binned according to the binning data corresponding to the TDI clock signal and further being specified by the TDI frequency control data and desired X-ray transmitted image is obtained (S9).

FIG. 11 shows a flow chart in which selection of self or other imaging mode and selection of high or normal speed imaging are done by mounting the X-ray imaging detector on the detector holder, however, such selection may be done automatically or manually or either mode may be fixed.

Figure 12:
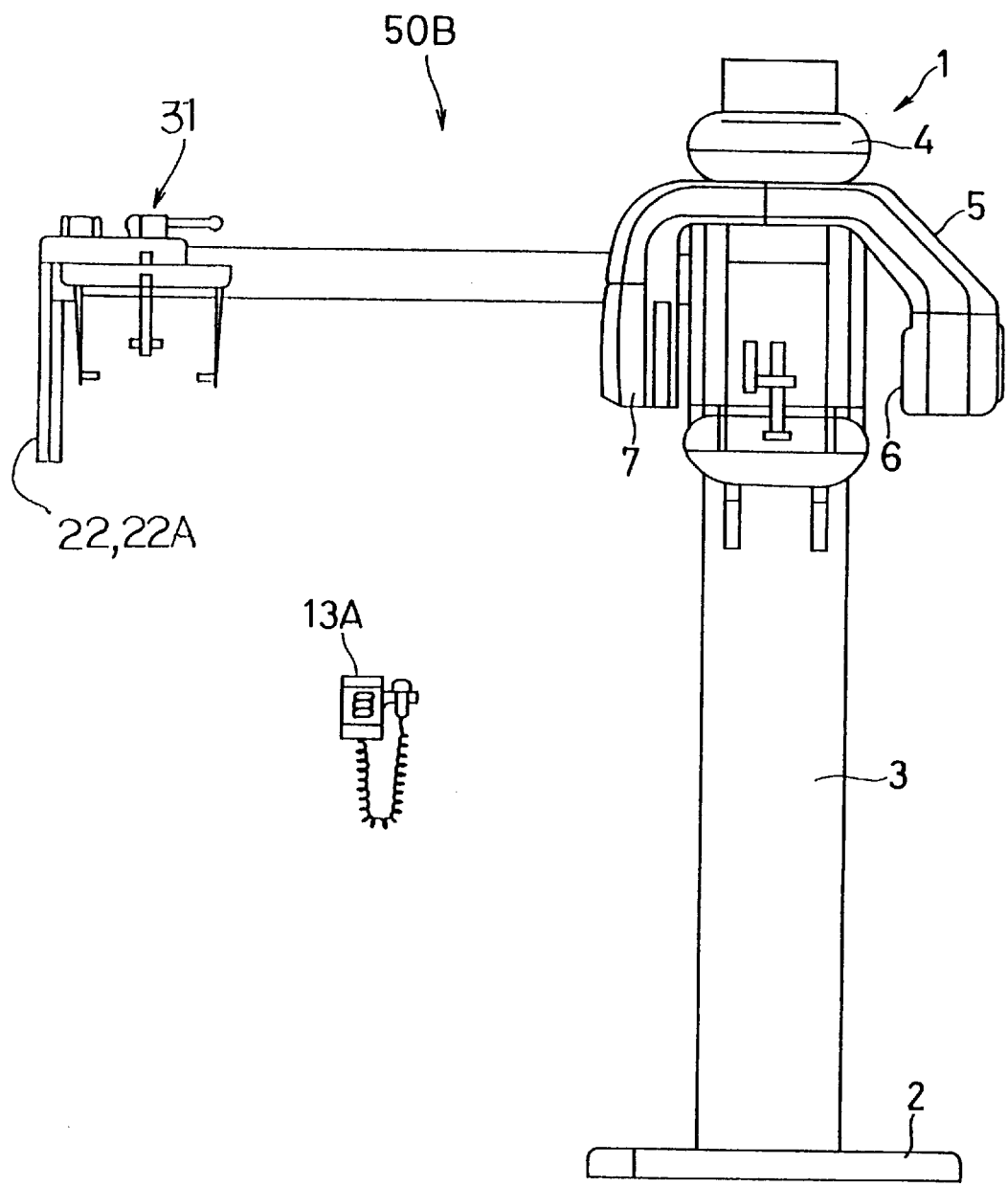
FIG. 12 shows outer front view of the other embodiment of the X-ray imaging apparatus having the X-ray imaging detector of the present invention.

FIG. 12 shows outer front view of the other embodiment of the X-ray imaging apparatus having the X-ray imaging detector of the present invention.

The X-ray imaging apparatus 50B is constructed as a cephalometric imaging apparatus in which X-ray imaging detectors 22, 22A and a support means 31 for fixing the head of the object in case of cephalometric imaging are further detachably provided for the X-ray imaging apparatus in FIG. 1 or the X-ray imaging apparatus in FIG. 10 so that such an apparatus can execute not only panoramic imaging but also cephalometric imaging. In such a case the same effect as mentioned in the imaging apparatus 50 and 50A can be brought out.

A remote control box 13A is the same as that 13 in FIG. 1, however, its setting position and operable contents are changed so as to be used for either panoramic and cephalometric imaging.

In case of cephalometric imaging, an X-ray detection part 7 is departed from the X-ray radiation area of the X-ray generator 6 and the X-ray from the X-ray generator 6 transmits through the head of the object fixed by the support means 31 so that it reaches the X-ray imaging detector 22, 22A. The detector 22, 22A is designed to be movable up and down or back and forth for the support means 31 for cephalometric imaging in such a manner that an X-ray receiving portion 25 receives the entire X-ray transmitted image of the object's head. The X-ray generator 6 is also designed to be movable up and down or back and forth in synchronism with the movement of the detector 22, 22A.

Figure 13:
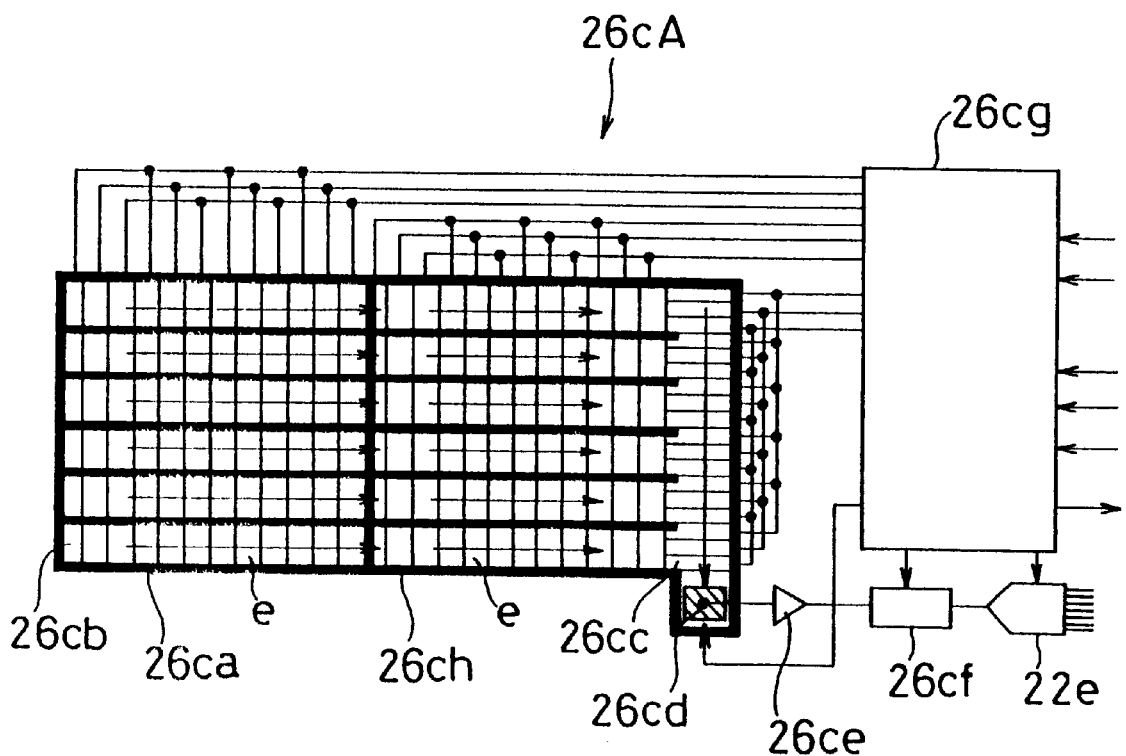
FIG. 13 shows schematic construction of the other embodiment of the imaging element provided for the X-ray imaging detector of the present invention.

FIG. 13 shows schematic construction of the other embodiment of the imaging element provided for the X-ray imaging detector of the present invention.

In FIG. 7 FFT type imaging element is used, however in the present invention, the above-mentioned associative shift register or output well may be added to FT (Frame Transfer) type CCD image sensor, IT (Interline Transfer) type CCD image sensor, or FIT (Frame Interline) type CCD image sensor.

FIG. 13 shows basic construction of the imaging element when FT type CCD image sensor is used.

According to the imaging element 26*c*A, it is different from the element 26*c* in FIG. 7 in that an accumulation part 26*ch* having pixel e like the sensor matrix 26*ca* is provided between the sensor matrix 26*ca* and the associative shift register 26*cc*. Other parts of both of them are the same.

According to the X-ray imaging detector, it is provided with the TDI clock generator and the TDI clock controller in its body and is a autonomic type detector of which imaging mode is such that imaging element can be TDI controlled without receiving supply of TDI clock signal from the X-ray imaging apparatus. Therefore, if the TDI clock generator isn't provided for the X-ray imaging apparatus, TDI imaging can be achieved so that the above-mentioned first object can be accomplished.

According to the X-ray imaging detector of the present invention, the TDI clock controller may be further provided with a clock control data memory storing the TDI frequency control data. In such an X-ray imaging detector, the TDI clock controller has the clock control data memory. Therefore, it is convenient that the TDI frequency control data which has been stored by a manufacturer beforehand can be taken out from the memory and TDI imaging can be executed.

According to the X-ray imaging detector of the present invention, further the clock control data memory may be rewritable and the TDI frequency control data can be rewritten by a manufacturer at the time of shipment in order to meet the product specification of the X-ray imaging apparatus. Therefore, it is convenient that appropriate TDI imaging can be executed in compliance with the X-ray imaging apparatus when an operator attaches the X-ray imaging detector on the X-ray imaging apparatus.

According to the X-ray imaging detector of the present invention, the clock control data memory may store plural patterns of the TDI frequency control data. In such an X-ray imaging detector, such control as enlarged imaging, maxillary antrum imaging, jaw joint imaging and selection of adult or child can be executed by storing plural patterns of TDI frequency control data in case of panoramic imaging using an X-ray imaging apparatus provided with an X-ray imaging detector. It is very convenient and can accomplish the above-mentioned third object.

According to the X-ray imaging detector of the present invention, TDI frequency control data can be selected by the selection means from the memory storing plural patterns of TDI clock signal so that the above-mentioned third object can be accomplished.

According to the X-ray imaging detector of the present invention, the TDI clock controller may be further provided with binning function so as to improve sensitivity of the sensor. As a result the data amount transferred to an A/D converter is reduced. Therefore, TDI controlled X-ray imaging can be achieved at high speed without replacing with high speed A/D converter and memory amount for processing picture image for X-ray imaging can be reduced so that the second object can be accomplished.

According to the above-mentioned imaging detector of the present invention, the electric charged image is integrated by binning and the electric charged image with enough contrast can be obtained by small amount of X-ray. Utilizing this, the X-ray generator and the X-ray imaging detector are moved at high speed and X-ray is radiated for a short time. Therefore, X-ray imaging can be executed at higher speed and X-ray exposed dose amount on the object can be reduced without changing the X-ray imaging apparatus itself. Furthermore, the problem of picture out of focus caused by movement of the object is resolved so that the above-mentioned second object can be accomplished.

According to the above-mentioned X-ray imaging detector of the present invention, it is convenient for an operator that normal projection mode and high speed imaging mode can be selectively executed and each imaging mode can be preferably executed because the frequency of the TDI clock signal and binning information are control element.

According to the above-mentioned X-ray imaging detector of the present invention, FFT (full frame transfer type) CCD censor is used as an imaging element. By using the characteristic of the sensor in which there is no accumulation part and a light receiving part is enlarged that much, it is preferably achieved for a measurement of slow frame rate, for example TDI X-ray imaging of the present invention.

The X-ray imaging apparatus of the present invention is provided with the above-mentioned detector so that the same effect as the above-mentioned detector can be achieved.

According to the X-ray imaging apparatus of the present invention, the TDI clock signal of the X-ray imaging detector is synchronized with movement control signal of the X-ray imaging apparatus so that X-ray imaging for executing TDI imaging can be preferably accomplished.

According to the X-ray imaging apparatus of the present invention, as the X-ray imaging apparatus is constructed as a panoramic imaging apparatus, the effect of the above-mentioned X-ray imaging apparatus can be brought out in case of panoramic imaging.

According to the X-ray imaging apparatus of the present invention, as the X-ray imaging apparatus is constructed as a cephalometric imaging apparatus, the effect of the above-mentioned X-ray imaging apparatus can be brought out in case of cephalometric imaging.

The X-ray imaging apparatus of the present invention is provided with the above-mentioned TDI clock generator, the above-mentioned TDI clock controller, the above-mentioned clock control data memory at the X-ray imaging apparatus side. And the TDI clock controller can execute high speed imaging using the above-mentioned binning operation. Therefore, if these parts are provided for the X-ray imaging detector, the apparatus can bring out the same effect as the above-mentioned detector so that high speed binning X-ray imaging apparatus of heteronomic type is achieved.

According to the X-ray imaging apparatus of the present invention, as it is provided with the same function of the above-mentioned X-ray imaging detector on the apparatus side so that the same effect of the X-ray imaging detector can be brought out even if such function isn't provided for the detector side.

According to the X-ray imaging apparatus of the present invention, imaging element is FFT type CCD sensor like the above-mentioned X-ray imaging detector so that the same effect as the X-ray imaging detector can be achieved.

According to the X-ray imaging apparatus of the present invention, the TDI clock signal of the X-ray imaging detector is synchronized with the movement control signal of the X-ray imaging apparatus so that TDI X-ray imaging can be preferably achieved.

According to the X-ray imaging apparatus of the present invention, as it is constructed as a panoramic imaging apparatus, the effect of the above-mentioned X-ray imaging apparatus can be brought out in case of panoramic imaging.

According to the X-ray imaging apparatus of the present invention, as it is constructed as a cephalometric imaging apparatus, the effect of the above-mentioned X-ray imaging apparatus can be brought out in case of cephalometric imaging.

What is claimed is:

1. An X-ray imaging detector for generating X-ray transmitted image in a form of electric signal, for use in X-ray imaging apparatus which comprises the X-ray imaging detector, an X-ray generator, and a fixing means for fixedly positioning an object to be examined between the X-ray generator and the X-ray imaging detector mounted thereon, whereby X-ray imaging is performed by moving the X-ray generator and the X-ray imaging detector both interposing the object fixedly positioned by the fixing means while keeping facing each other, said X-ray imaging detector comprising:

an imaging element for generating electric charged image constituting X-ray transmitted image by detecting X-ray radiated from said X-ray generator and transmitted through said object, a TDI (Time Delay Integration) clock generator for generating TDI clock signal, and a TDI clock controller for controlling generating of TDI clock signal from said TDI clock generator based on TDI frequency control data for controlling the frequency of the TDI clock signal and for executing TDI control of the electric charged image generated by said imaging element corresponding to said TDI clock signal, and wherein:

said TDI clock controller is provided with a clock control data memory storing said TDI frequency control data, and said clock control data memory rewritably stores said TDI frequency control data.

2. An X-ray imaging detector for generating X-ray transmitted image in a form of electric signal, for use in X-ray imaging apparatus which comprises the X-ray imaging detector, an X-ray generator, and a fixing means for fixedly positioning an object to be examined between the X-ray generator and the X-ray imaging detector mounted thereon, whereby X-ray imaging is performed by moving the X-ray generator and the X-ray imaging detector both interposing the object fixedly positioned by the fixing means while keeping faring each other, said X-ray imaging detector comprising:

an imaging element for generating electric charged image constituting X-ray transmitted image by detecting X-ray radiated from said X-ray generator and transmitted through said object, a TDI clock generator for generating TDI clock signal, and a TDI clock controller for controlling generating of TDI clock signal from said TDI clock generator based on TDI frequency control data for controlling the frequency of the TDI clock signal and for executing TDI control of the electric charged image generated by said imaging element corresponding to said TDI clock signal, and wherein:

said TDI clock controller is provided with a clock control data memory storing said TDI frequency control data, and said clock control data memory stores plural patterns of said TDI frequency control data.

3. The X-ray imaging detector as set forth in claim 2, wherein a selection means for selecting at least one of said plural patterns of TDI frequency control data stored in said clock control data memory is further provided.

4. An X-ray imaging detector for generating X-ray transmitted image in a form of electric signal, for use in X-ray imaging apparatus which comprises the X-ray imaging detector, an X-ray generator, and a fixing means for fixedly positioning an object to be examined between the X-ray generator and the X-ray imaging detector mounted thereon, whereby X-ray imaging is performed by moving the X-ray generator and the X-ray imaging detector bath interposing the abject fixedly positioned by the fixing means while keeping facing each other, said X-ray imaging detector comprising:

an imaging element for generating electric charged image constituting X-ray transmitted image by detecting X-ray radiated from said X-ray generator and transmitted through said object, a TDI clock generator for generating TDI clock signal, and a TDI clock controller for controlling generating of TDI clack signal from said TDI clock generator based on TDI frequency control data for controlling the frequency of the TDI clock signal and for executing TDI control of the electric charged image generated by said imaging element corresponding to said TDI clock signal, and wherein:

said TDI clock controller further has binning processing function when the electric charged image generated by said imaging element is processed by TDI control method, and said TDI clock controller can selectively execute at least normal projection mode and high-speed projection mode which is faster than the normal mode when said electric charged image generated by said imaging element is processed by TDI control method and wherein in each projection mode, frequency of said TDI clock signal and binning data are employed as control elements.

5. An X-ray imaging detector for generating X-ray transmitted image in a form of electric signal, for use in X-ray imaging apparatus which comprises the X-ray imaging detector, an X-ray generator, and a fixing means for fixedly positioning an object to be examined between the X-ray generator and the X-ray imaging detector mounted thereon, whereby X-ray imaging is performed by moving the X-ray generator and the X-ray imaging detector both interposing the object fixedly positioned by the fixing means while keeping facing each other, said X-ray imaging detector comprising:

an imaging element for generating electric charged image constituting X-ray transmitted image by detecting X-ray radiated from said X-ray generator and transmitted through said object, a TDI clock generator for generating TDI clock signal, and a TDI clock controller for controlling generating of TDI clock signal from said TDI clock generator based on TDI frequency control data for controlling the frequency of the TDI clock signal and for executing TDI control of the electric charged image generated by said imaging element corresponding to said TDI clock signal, and wherein:

said TDI clock controller has further function of moving said X-ray generator and said X-ray imaging detector at high speed while keeping facing each other by executing binning process when said electric charged image generated by said imaging element corresponding to said TDI clock signal is processed by TDI control method, and said TDI clock controller can selectively execute at least normal projection mode and high-speed projection mode which is faster than the normal mode when said electric charged image generated by said imaging element is processed by TDI control method and wherein in each projection mode, frequency of said TDI clock signal and binning data are employed as control elements.

6. The X-ray imaging detector as set forth in any one of claims 4 and 5, wherein an imaging element for producing X-ray transmitted image is a CCD sensor of full frame transfer type.

7. An X-ray imaging apparatus comprising an X-ray imaging detector, an X-ray generator, and a fixing means for fixedly positioning an abject to be examined between the X-ray generator and the X-ray imaging detector mounted thereon, whereby X-ray image is produced by moving the X-ray generator and the X-ray imaging detector both interposing the object fixedly positioned by the fixing means while keeping facing each other, wherein said X-ray imaging detector comprises an imaging element for producing electric charged image constituting X-ray transmitted image by detecting X-ray radiated from said X-ray generator and transmitted through said object, wherein said X-ray imaging apparatus comprises:

a TDI clock generator for generating TDI clock signal, a clock control data memory storing TDI frequency control data for controlling frequency of TDI clock signal generated from said TDI clock generator, and a TDI clock controller for controlling generating of TDI clock signal from said TDI clock generator based on TDI frequency control data for controlling the frequency of the TDI clock signal and for executing TDI control of the electric charged image generated by said imaging element corresponding to said TDI clock signal, and wherein:

said TDI clock controller has function of moving said X-ray generator and said X-ray imaging detector at high speed while keeping facing each other by executing binning processing when said electric charged image generated by said imaging element corresponding to said TDI clock signal is processed by TDI control method, and said TDI clock controller can selectively execute at least normal projection mode and high-speed projection mode which is faster than the normal mode when said electric charged image generated by said imaging element is TDI controlled and wherein in each projection mode frequency of said TDI clock signal and binning data are employed as control elements.

8. The X-ray imaging apparatus as set forth in claim 7, wherein an imaging element for producing X-ray transmitted image is a CCD sensor of full frame transfer type.

9. The X-ray imaging apparatus as set forth in any one of claims 7 and 8, wherein the TDI clock signal generated from said TDI clock generator provided for said X-ray imaging apparatus and movement control signal for moving said X-ray generator and the X-ray imaging detector both interposing the object fixedly positioned by said fixing means while keeping facing each other are varied in synchronizing manner.

10. The X-ray imaging apparatus as set forth in any one of claims 7 and 8, wherein said X-ray imaging apparatus is a panoramic X-ray imaging apparatus.

11. The X-ray imaging apparatus as set forth in any one of claims 7 and 8, wherein said X-ray imaging apparatus is a cephalometric X-ray imaging apparatus.

* * * * *